US 6,658,917 B2

(12) United States Patent
Kim et al.

(10) Patent No.: US 6,658,917 B2
(45) Date of Patent: Dec. 9, 2003

(54) AIR-SAMPLING CARRIER, APPARATUS AND METHOD FOR ANALYZING AIR IN A SEMICONDUCTOR PROCESS TOOL (75) Inventors: Tae-Ho Kim, Seoul (KR); Dong-Seok Ham, Suwon-si (KR)

(73) Assignee: Samsung Electronics Co., Ltd., Kyungki-do (KR)

( * ) Notice: Subject to any disclaimer, the term of this patent is extended or adjusted under 35 U.S.C. 154(b) by 0 days.

(21) Appl. No.: 10/145,807

(22) Filed: May 16, 2002

(65) Prior Publication Data

US 2002/0174709 A1 Nov. 28, 2002

(30) Foreign Application Priority Data

May 17, 2001 (KR) ........................ 2001-27069

(51) Int. Cl.[7] .................. G01N 1/22; G01N 21/72; B05C 5/00; B44C 1/22; C03C 15/00
(52) U.S. Cl. .............. 73/31.01; 73/23.2; 73/31.02; 156/345.32
(58) Field of Search .............. 73/31.01, 31.02, 73/23.2, 31.06; 156/345.32; 118/729

(56) References Cited

U.S. PATENT DOCUMENTS

| 4,816,098 | A | * | 3/1989 | Davis et al. | 156/345 |
|---|---|---|---|---|---|
| 5,074,137 | A | * | 12/1991 | Harris et al. | 73/31.02 |
| 5,184,502 | A | * | 2/1993 | Adams et al. | 73/31.01 |
| 5,297,421 | A | * | 3/1994 | Hosonuma et al. | 73/40 |
| 5,356,594 | A | * | 10/1994 | Neel et al. | 422/54 |
| 5,406,265 | A | * | 4/1995 | Trozzo et al. | 340/632 |
| 5,440,916 | A | * | 8/1995 | Stone et al. | 73/23.31 |
| 5,554,846 | A | * | 9/1996 | Regiec et al. | 250/288 |
| 5,604,299 | A | * | 2/1997 | Cobb | 73/31.02 |
| 5,708,218 | A | * | 1/1998 | Jax | 73/863.23 |
| 5,725,664 | A | * | 3/1998 | Nanbu et al. | 118/52 |
| 5,742,516 | A | * | 4/1998 | Olcerst | 364/496 |
| 5,949,341 | A | * | 9/1999 | Oliver | 340/626 |
| 6,114,964 | A | * | 9/2000 | Fasano | 340/632 |
| 6,212,937 | B1 | * | 4/2001 | Hubert et al. | 73/23.2 |
| 6,332,349 | B1 | * | 12/2001 | Poynot | 73/23.2 |

* cited by examiner

Primary Examiner—Hezron Williams
Assistant Examiner—David J. Wiggins
(74) Attorney, Agent, or Firm—Lee & Sterba, P.C.

(57) ABSTRACT

An air-sampling carrier for sampling air from a clean room of a semiconductor processing facility, an apparatus and a method for analyzing the air, wherein the air-sampling carrier includes a container having an inner space, a door mounted at a front wall of the container, a discharging pipe for discharging the air sample out of the container, and at least one inlet tube for introducing purge gas into the inner space of the container from outside the container. The discharging pipe and inlet tube are respectively formed on an outer surface of the container and connected to an inner space of the container. The air in the unit process tools is effectively sampled using an unmanned carrying apparatus and the pollution level of the air sample is simply and easily measured.

11 Claims, 7 Drawing Sheets

AIR-SAMPLING CARRIER, APPARATUS AND METHOD FOR ANALYZING AIR IN A SEMICONDUCTOR PROCESS TOOL

BACKGROUND OF THE INVENTION

1. Field of the Invention

The present invention relates to an air-sampling carrier and an apparatus and a method for analyzing air of semiconductor fabricating facilities. More particularly the present invention relates to an air-sampling carrier having an exterior shape similar to that of a wafer carrier, and an apparatus and method for efficiently performing a cleanness inspection of respective unit process tools having a plurality of high immaculacy clean rooms and disposed in semiconductor fabricating lines.

2. Description of the Related Art

As semiconductor fabricating facilities are adapted to fabricate wafers having a diameter of 300 mm, an automatic material handling system (AMHS) and a computer integrated manufacturing (CIM) system have been adopted in the semiconductor fabricating facilities to provide 300 mm wafer lots to an inter-bay (BAT TO BAY) or an intra-bay (TOOL TO TOOL).

The unmanned automatic facilities mentioned above include a wafer carrier, a front opening unified pod (hereinafter referred to as a "FOUP"), and an unmanned carrying apparatus such as an OHT (overhead transfer) system, an OHC (overhead conveyor) system or an AGV (automatic guided vehicle).

Each unit process tool includes a load port for installing the FOUP at a front portion thereof, and a door opener for opening and closing a front door of the FOUP. Accordingly, a wafer is loaded onto the respective unit process tool or unloaded from the respective unit process tool after opening the door of the FOUP.

Therefore, an independently controlled Mini-environment system is usually installed to each unit process tool to simulate a high immaculacy clean room. Product quality is improved due to a partially high immaculacy space provided by the Mini-environment system.

The Mini-environment system is required to be controlled independently of an exterior environment, and therefore almost all outer walls of the Mini-environment system are fully sealed from the exterior environment. Therefore, in order to monitor an inner state of the Mini-environment system, the Mini-environment system must be equipped with various sensors for comparing actual data with a managerial criteria in order to detect an unstable or unusual inner state of the Mini-environment system.

However, three hundred or more Mini-environment systems are commonly required to fabricate a semiconductor device. When a management item is added, each Mini-environment system requires a sensor for detecting the management item. Consequently, as the number of management items is increased, the number of sensors to be installed to all of the Mini-environment systems is dramatically increased, which may make operation of the Mini-environment systems impossible.

Furthermore, when atmospheric pollution in the semiconductor fabricating facilities is estimated, either many analyzers are used individually for estimating a specific pollution matter, or alternatively, many operators are required to analyze various pollution matters using only one analyzer. Also, more time and many more operators are necessary when a system is required to perform periodic estimations of the pollution level.

SUMMARY OF THE INVENTION

The present invention has been made to solve the aforementioned problems. Accordingly, it is a feature of an embodiment of the present invention to provide an air-sampling carrier for effectively sampling air in a high immaculacy clean room of a respective unit process tool by means of carrying a container having a similar exterior shape as a wafer carrier to the respective unit process tool by using an unmanned carrying apparatus.

It is another feature of an embodiment of the present invention to provide an apparatus and a method for analyzing air sampled by the air-sampling carrier.

In order to provide these and other features of the present invention, according to one embodiment of the present invention, an air-sampling carrier is provided including: a container having an inner space; a door mounted at a front wall of the container; a discharging pipe, which is formed on an outer surface of the container and is connected to an inner space of the container, for discharging sampled air out of the container; and at least one inlet tube, which is formed on the outer surface of the container and connected to the inner space of the container, for introducing purge gas into the inner space of the container from outside the container.

Preferably, the air-sampling carrier has an external appearance according to a FOUP (front opening unified pod) standard.

According to another embodiment of the present invention, an apparatus for analyzing air for use in semiconductor fabricating facilities is provided, having a closed type wafer carrier, a plurality of respective unit process tools for opening and closing a door of the closed type wafer carrier and for loading and unloading wafers, and an unmanned carrying apparatus for carrying the closed type wafer carrier to the respective unit process tools. The apparatus includes: an air-sampling carrier for sampling air inside the respective unit process tools having an external appearance similar to that of the closed type wafer carrier to facilitate being carried by the unmanned carrying apparatus; and an air analyzer for analyzing the air inside the air-sampling carrier in order to measure a pollution level of the air from inside the respective unit process tools sampled by the air-sampling carrier.

In another embodiment of the present invention, the air analyzer may include a support for supporting the air-sampling carrier; a sample port line connected to the discharging pipe of the air-sampling carrier placed on the support to introduce the sampled air therein; a purge gas supplying line connected to at least one inlet tube of the air-sampling carrier placed on the support to supply the purge gas; and an analyzer, which is connected to the sample port line, for analyzing a pollution level of the sampled air.

According to another embodiment of the present invention, a method of analyzing air in semiconductor fabricating facilities includes: transporting an air-sampling carrier by means of an unmanned carrying apparatus to a respective unit process tool in which the air is to be sampled; sampling the air in the respective unit process tool by introducing the air into an inner carrier of the air-sampling carrier after opening a door of the air-sampling carrier; transporting the air-sampling carrier to an air analyzer by means of the unmanned carrying apparatus; connecting a sample port line and a purge gas supplying tube of the air analyzer to the air-sampling carrier; analyzing a pollution level of the sampled air after introducing the sampled air and purge gas into the air analyzer through the sample port line while injecting the purge gas into an inner space of the air-sampling carrier through the purge gas supplying line; and providing the inner space of the air-sampling carrier with a purge gas having a pollution level of zero through the purge gas supplying line after disconnecting the sample port line from the air-sampling carrier when the analyzing is finished.

BRIEF DESCRIPTION OF THE DRAWINGS

The above and other features and advantages of the present invention will become readily apparent to one of ordinary skill in the art by reference to the following detailed description when considered in conjunction with the accompanying drawings in which.

DETAILED DESCRIPTION OF THE INVENTION

Korean Patent Application No. 2001-27069, filed on May 17, 2001, and entitled: "Air-Sampling Carrier, Apparatus and Method for Analyzing Air in a Semiconductor Process Tool" is incorporated by reference herein in its entirety.

Hereinafter, the present invention will be described in detail with reference to the accompanying drawings.

Figure 1:
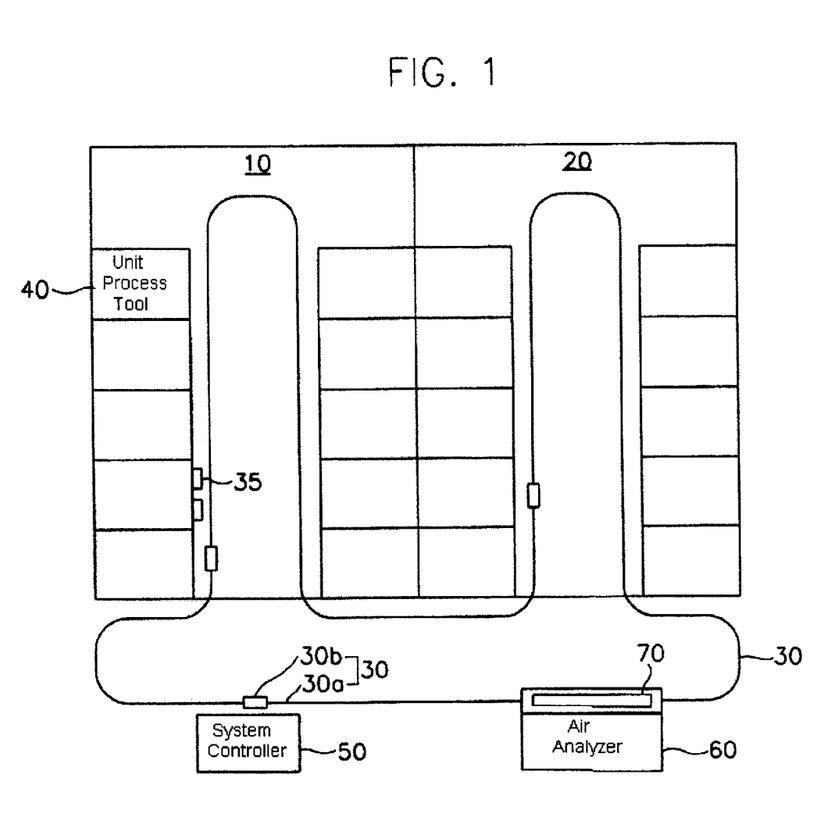
FIG. 1 illustrates a schematic view of an automatic unmanned semiconductor fabricating facility having an air analyzing apparatus according to an embodiment of the present invention.

FIG. 1 illustrates a schematic view of an automatic unmanned semiconductor fabricating facility having an air analyzing apparatus according to an embodiment of the present invention.

Referring to FIG. 1, a first bay 10 and a second bay 20 are connected by means of an unmanned carrying apparatus 30 in the semiconductor fabricating facility. A plurality of unit process tools 40 are respectively disposed in a line of two rows facing each other in each bay.

The unmanned carrying apparatus 30 is an OHT (overhead transfer) system or an OHC (overhead conveyor) system, in which an unmanned carrier 30b moves along a rail 30a to transfer a wafer carrier 35 to a respective unit process tool 40 in each of the first and second bays 10 and 20.

The wafer carrier 35 is preferably a closed vessel according to a FOUP (front opening unified pod) standard. The FOUP has a box shape including a door at a front wall and generally receives thirteen to twenty-five wafers having a size of 300 mm. During transportation of the wafer, a door of the wafer carrier 35 is closed, thereby preventing pollution of the wafer. Externally, the wafer carrier 35 is designed to perform an unmanned transportation controlled by a computer system.

A system controller 50 causes the unmanned carrier 30b to move to a desired position, carrying the wafer carrier 35 with it. The system controller 50 causes the unmanned carrier 30b to return to the original position, bringing with it the wafer carrier 35 including a processed wafer. The system controller 50 is connected to various respective unit process tools in a network so that the system controller 50 receives data of a processing state from the respective unit process tools 40, and operates the unmanned carrier 30b to provide the wafer carrier 35 to the respective unit process tools 40 requiring the wafers.

When an arrival signal of the unmanned carrier 30b is received from the respective unit process tools 40, the system controller 50 places the wafer carrier 35 transported by the unmanned carrier 30b on a load port of the respective unit process tool 40 and lifts up the wafer carrier 35 placed on the load port of the respective process tool 40.

In the present invention for use in semiconductor fabricating facilities, an air analyzer 60 is installed to the unmanned carrying apparatus 30. An air-sampling carrier 70, which is reconstructed from the wafer carrier 35, may be attached to the unmanned carrying apparatus 30, in which case the air-sampling carrier 70 is transported instead of the wafer carrier 35 to the respective unit process tools 40. The air-sampling carrier 70 samples the air in clean rooms of the respective unit process tools 40. After sampling an air sample, the air-sampling carrier 70 is made to move to an air analyzer 60 by the system controller 50.

Figure 2:
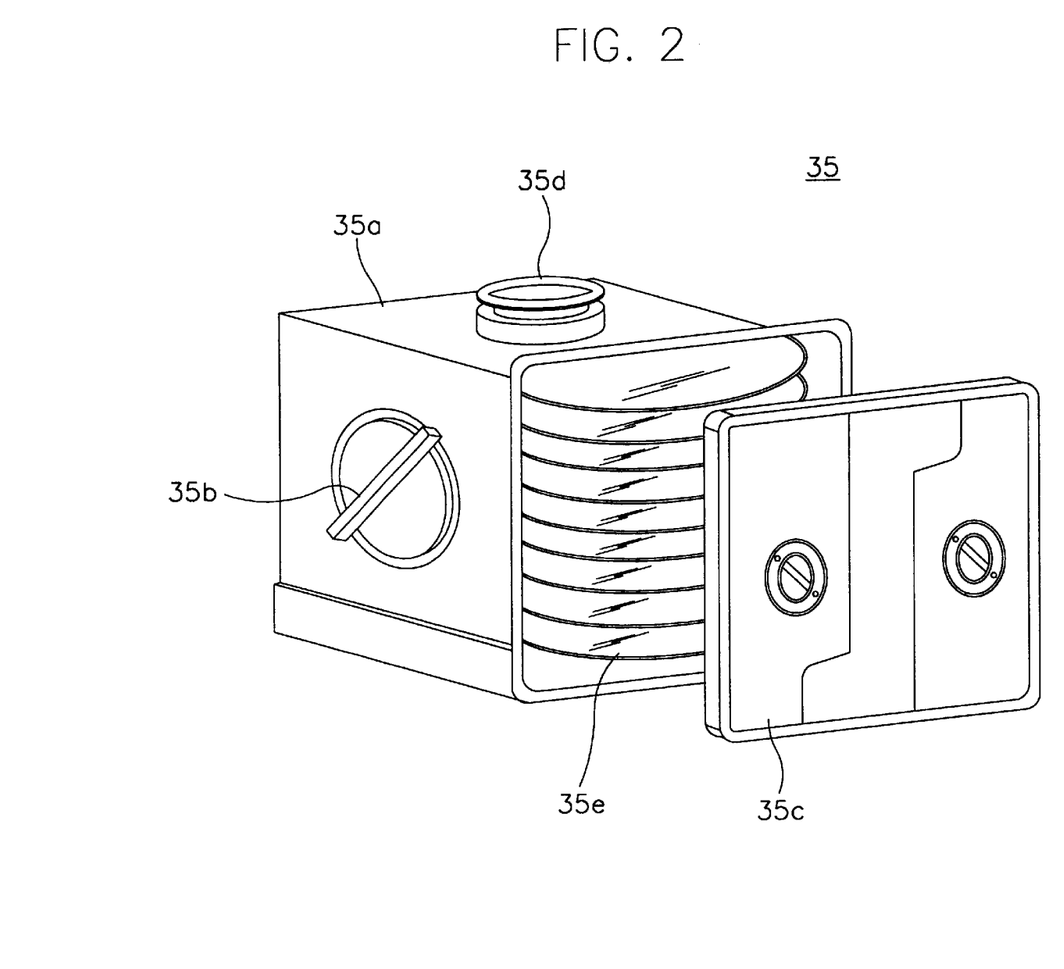
FIG. 2 illustrates a schematic view showing a construction of a closed type wafer carrier used in the semiconductor fabricating facility shown in FIG. 1.
Figure 3:
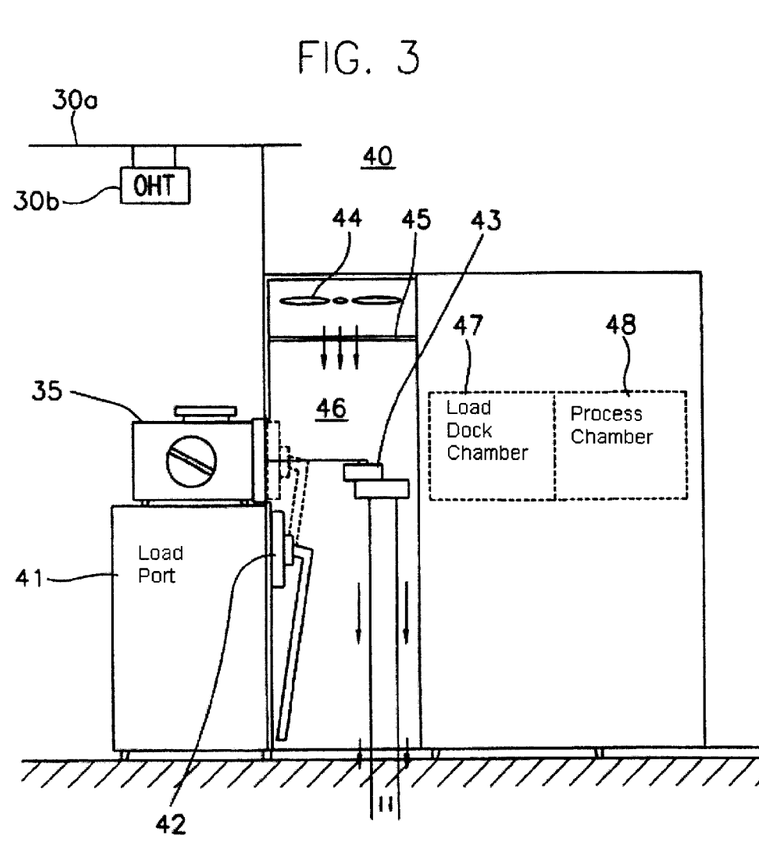
FIG. 3 illustrates a schematic view showing a construction of a respective unit process tool including a Mini-environment system used in the semiconductor fabricating facility shown in FIG. 1.

Referring to FIGS. 2 and 3, the wafer carrier 35 has a box type housing 35a including an open front side and a door 35c detachably installed at the front side of the housing 35a. The door 35c is installed at the front side of the housing 35a by a locking device, and is separated from the housing 35a when the locking device is released by a door opener having a key. Handle grips 35b are attached to both sides of the housing 35a to facilitate carrying the wafer carrier 35, and a knob 35d is installed on a top surface of the housing 35a so that the unmanned carrier 30b can lift up the wafer carrier 35.

A plurality of gates corresponding to the door 35c of the wafer carrier 35 are formed at a respective front side of the respective unit process tools 40. Generally, the gates are closed by a door opener 42. The wafer carrier 35 is positioned on the load port 41 by the unmanned carrier 30b. When the wafer carrier 35 is placed on a top surface of the load port 41, the wafer carrier 35 is moved to a front of the respective unit process tool 40 to face the gate of the respective unit process tool 40.

Then, the door opener 42 opens the door 35c of the wafer carrier 35 and moves downwardly with the door 35c of the wafer carrier 35. Accordingly, the gates are isolated from the external environment by the housing of the wafer carrier 35, but the wafer carrier 35 is opened, thereby exposing the wafers therein, so that the wafers may be loaded into the respective unit process tools 40.

A front chamber of a respective unit process tool 40 is a high immaculacy clean room 46, in which an air shower device is mounted to keep the clean room highly immaculate. The air shower device includes a fan 44 mounted on an upper wall of the respective unit process tool 40 and a filter 45. Accordingly, the front chamber of the clean room 46 of the respective unit process tools 40 is more immaculate than an exterior clean room in which the wafer carrier 35 is moved.

Furthermore, a transfer robot 43 is disposed in the clean room 46 of the respective unit process tools 40 to load the wafers 35e received in the wafer carrier 35 into a load lock chamber 47 or to unload the wafers from the load lock chamber 47 into the wafer carrier 35.

A process chamber 48 is disposed at a rear portion of the load lock chamber 47 in the respective unit process tools 40.

More specifically, the respective unit process tools 40 are operated under a Mini-environment system that is a high immaculacy clean room. Thus, a pollution level of the Mini-environment system must be measured and controlled.

Since the Mini-environment system is required to be controlled independently of an exterior environment due to a characteristic thereof, almost all the outer walls of the respective unit process tools 40 are fully sealed from the exterior environment. Therefore, in order to detect an unstable or unusual inner state of the Mini-environment system, various kinds of sensors conforming to a managerial criteria are installed in the respective unit process tools 40, and an inner state of the respective unit process tools 40 is monitored.

However, three hundred or more sets of Mini-environment systems are commonly required to fabricate a semiconductor device. When a management item is added, a sensor for detecting the management item is to be installed to each Mini-environment system. Consequently, as the number of management items increases, the number of sensors to be installed to each of the Mini-environment systems is dramatically increased, which makes operation of the Mini-environment systems impossible.

Furthermore, when estimating atmospheric pollution in the semiconductor fabricating facility, either many analyzers are used individually for estimating a specific pollution matter, or alternatively, many operators are required to analyze various pollution matters using only one analyzer. Additionally, more time and many more operators are necessary when a system is required to perform periodic estimations of the pollution level.

Figure 4:
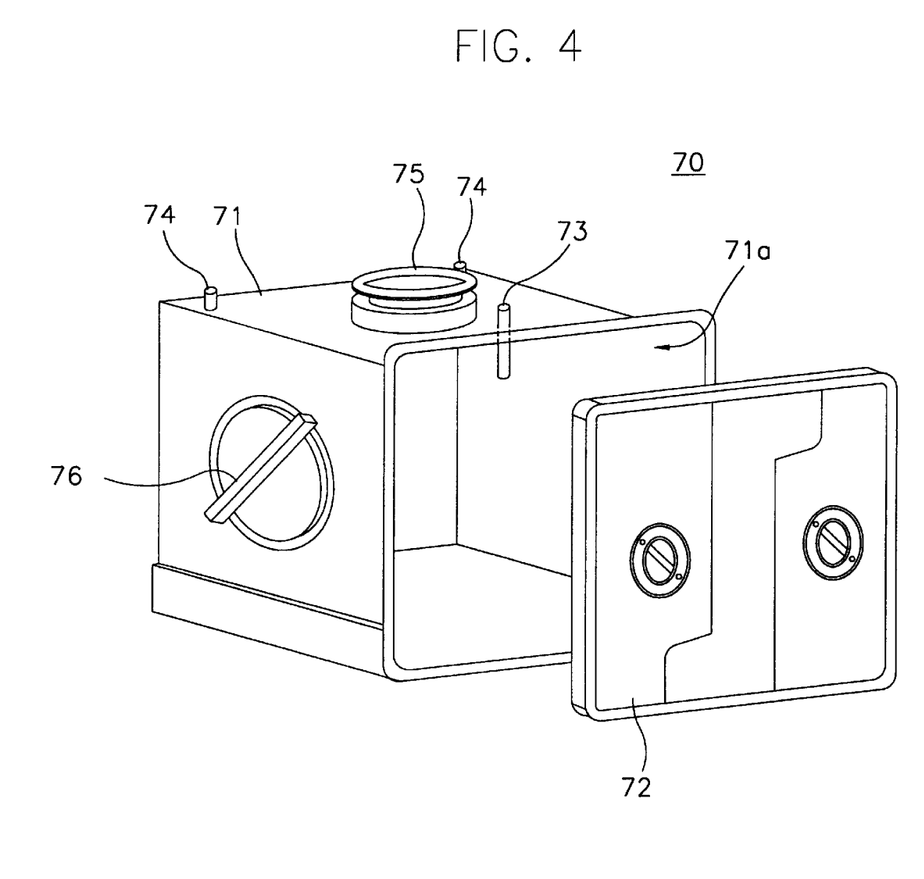
FIG. 4 illustrates a perspective view showing an air-sampling carrier according to an embodiment of the present invention.
Figure 5:
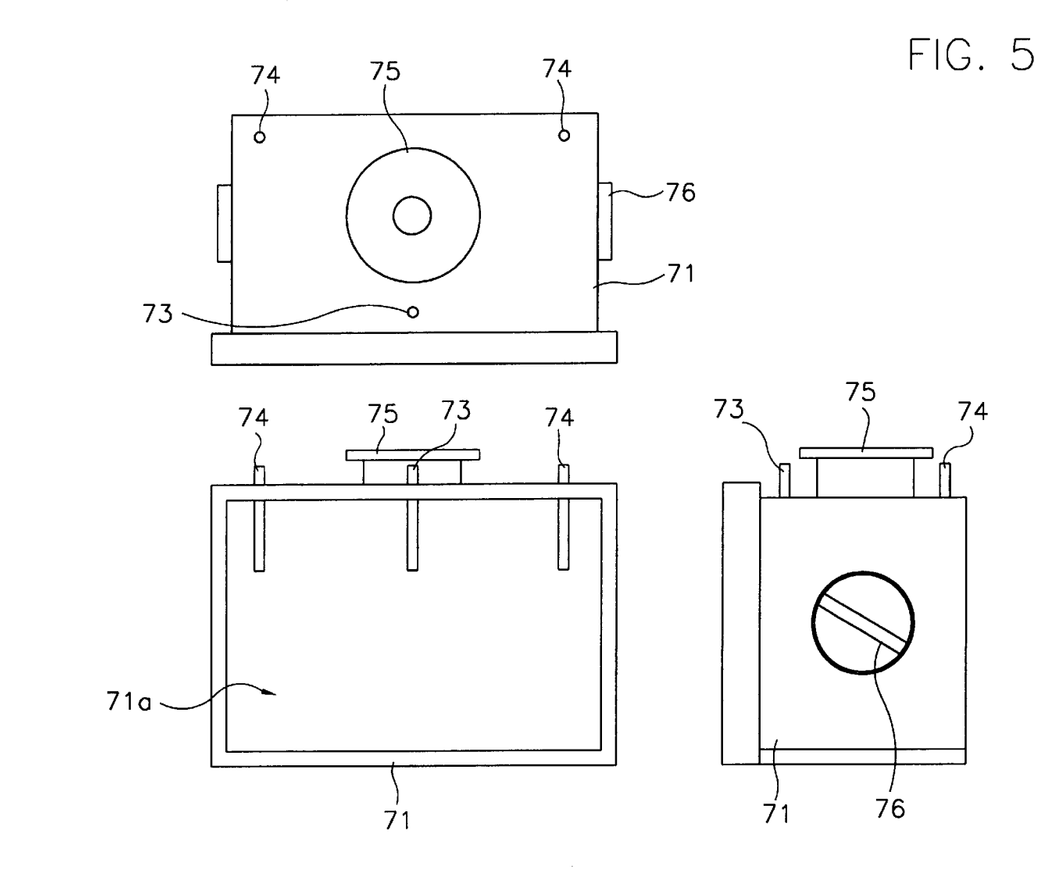
FIG. 5 illustrates a view of a construction of the air-sampling carrier shown in FIG. 4.

FIGS. 4 and 5 illustrate views showing the air-sampling carrier according to an embodiment of the present invention.

According to an embodiment of the present invention, the air-sampling carrier 70 has basically a FOUP shape, and has no wafer slots or other internal structures, with the exception of an end of a discharging pipe and ends of one or more inlet tubes.

The air-sampling carrier 70 has a box type housing, i.e. a container 71 having an inner space 71a, and an opening door 72 installed at a front side of the container 71. The opening door 72 has the same shape and size as the door of the wafer carrier (35 of FIG. 1), but a sealing material, such as rubber, is preferably attached to a front side of the air-sampling carrier 70 in order to keep an airtight seal between the air-sampling carrier 70 and the respective unit process tools (40 of FIG. 1).

In addition, a discharging pipe 73 is mounted in an upper wall of the container 71 at a center portion of a front side thereof, to communicate with the inner space 71a and to discharge the sampled air out of the air-sampling carrier 70. Further, preferably two inlet tubes 74 are respectively installed at each corner of a rear side in the upper wall of the container 71 to communicate with the inner space 71a and to introduce purge gas into the inner space 71a. One end of the discharging pipe 73 and one end of the inlet tubes 74 preferably extend to an intermediate height of the inner space 71a.

The discharging pipe 73 is preferably installed to be adjacent to the door rather than the rear portion of the inner space since the air of the clean room is introduced through the opening door of the air-sampling carrier 70 into the inner space 71a.

It is preferable to mount the inlet tubes 74 at corners of the inner rear portion in the inner space 71a to provide the sampled air to the air analyzer more effectively.

Furthermore, the discharging pipe 73 and the two inlet tubes 74 each have a valve at an intermediate portion thereof to be opened and closed by air pressure. The valves are normally closed to prevent exterior pollution matter from entering the inner space 71a of the air-sampling carrier 70.

The valve of the discharging pipe 73 opens outwardly when the air pressure in the inner space 71a increases and the valves of the inlet tubes 74 open inwardly when the air pressure in the inlet tubes 74 is higher than that of the inner space 71a.

Meanwhile, the container 71 has a knob 75 installed on the upper wall thereof, which has the same shape and size as those of the wafer carrier (35 of FIG. 2) so that the unmanned carrier 30b can hold the container 71. The container 71 also has handle grips 76 mounted on the sidewalls thereof.

Figure 6:
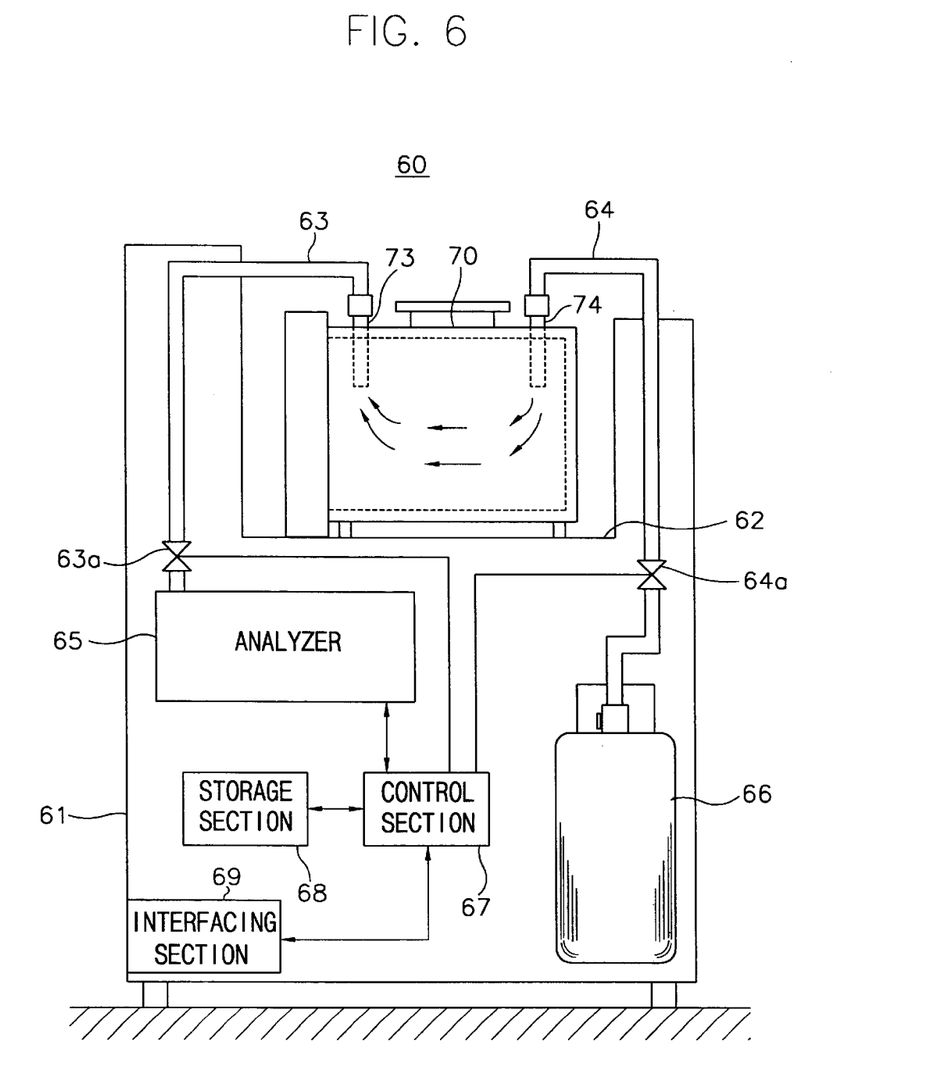
FIG. 6 illustrates a schematic view showing a construction of an air analyzer according to an embodiment of the present invention.

Referring to FIG. 6, according to an embodiment of the present invention, an air analyzer 60 has a general box type housing 61 on which a support 62 is placed to support the air-sampling carrier 70.

Furthermore, the air analyzer 60 has a sample port line 63, which is connected to the discharging pipe 73 of the air-sampling carrier 70 placed on the support 62, for receiving the air sample, and two purge gas supplying lines 64, which are connected to both sides of an upper surface of the inlet tubes 74, for supplying a purge gas.

The air analyzer 60 includes an analyzer 65 for analyzing the pollution level of the air sample introduced therein, which is connected to the sample port line 63, a purge gas supplying vessel 66, a control section 67, a storage section 68 and an interfacing section 69.

The control section 67 controls the opening and closing of the valve 63a installed in the sample port line 63 and the valve 64a installed in the purge gas supplying tube 64. The control section 67 receives data relating to the pollution level measured by the analyzer 65, and stores the data in a sample file in the storage section 68. Furthermore, the control section 67 is connected through the interface section 69 to the system controller (50 of FIG. 1) to transfer the measured data to the system controller 50 or to receive the data from the system controller 50.

The discharging pipe 73 and the inlet tubes 74 are respectively connected to the sample port line 63 and the purge gas supplying tube 64. The control section 67 controls the analyzer 65 to analyze the pollution level of the air sample while the valve 64a is opened so that the purge gas is supplied through the purge gas supplying line 64 to the inner space of the air-sampling carrier 70 and the valve 63a is opened so that the air sample and the purge gas are provided through the sample port line 63 to the analyzer 65. The purge gas may be nitrogen gas or dry air having a pollution level of zero. Therefore, the air introduced into the inner space of the air-sampling carrier 70 is supplied such that the air adjacent to the door of the air-sampling carrier 70 is supplied to the analyzer 65 first, and the air adjacent to the corners of the air-sampling carrier 70 is supplied to the analyzer 65 last.

Here, the sample port line and the purge gas supplying line are manually or automatically connected with the air-sampling carrier 70, but automatic connection using an electric motor is preferred.

After the analyzing is finished, the control section 67 allows the valve 63*a* to be closed and causes the sample port line 63 to be separated from the discharging pipe 73 while the purge gas is introduced through the purge gas supplying line 64 into the air-sampling carrier 70 to clean and charge the inner space 71*a* of the air-sampling carrier 70 with the purge gas.

The air analyzer 60 calculates the pollution level by the following equation:

$$\text{pollution level of the respective unit process tools} = \frac{a \times (b + c)}{d}$$

where a denotes a pollution level in the air analyzer, b denotes a volume of the air-sampling carrier, c denotes an injection volume of the purge gas, and d denotes a volume of the air-sampling carrier.

The door at the front side of the air-sampling carrier 70 is opened only for performing the sampling of air in the process tools and closed for performing other operations.

The calculated pollution level is preferably filed with identification information relating to the clean room and converted to a database to be stored in the storage section 67.

Figure 7:
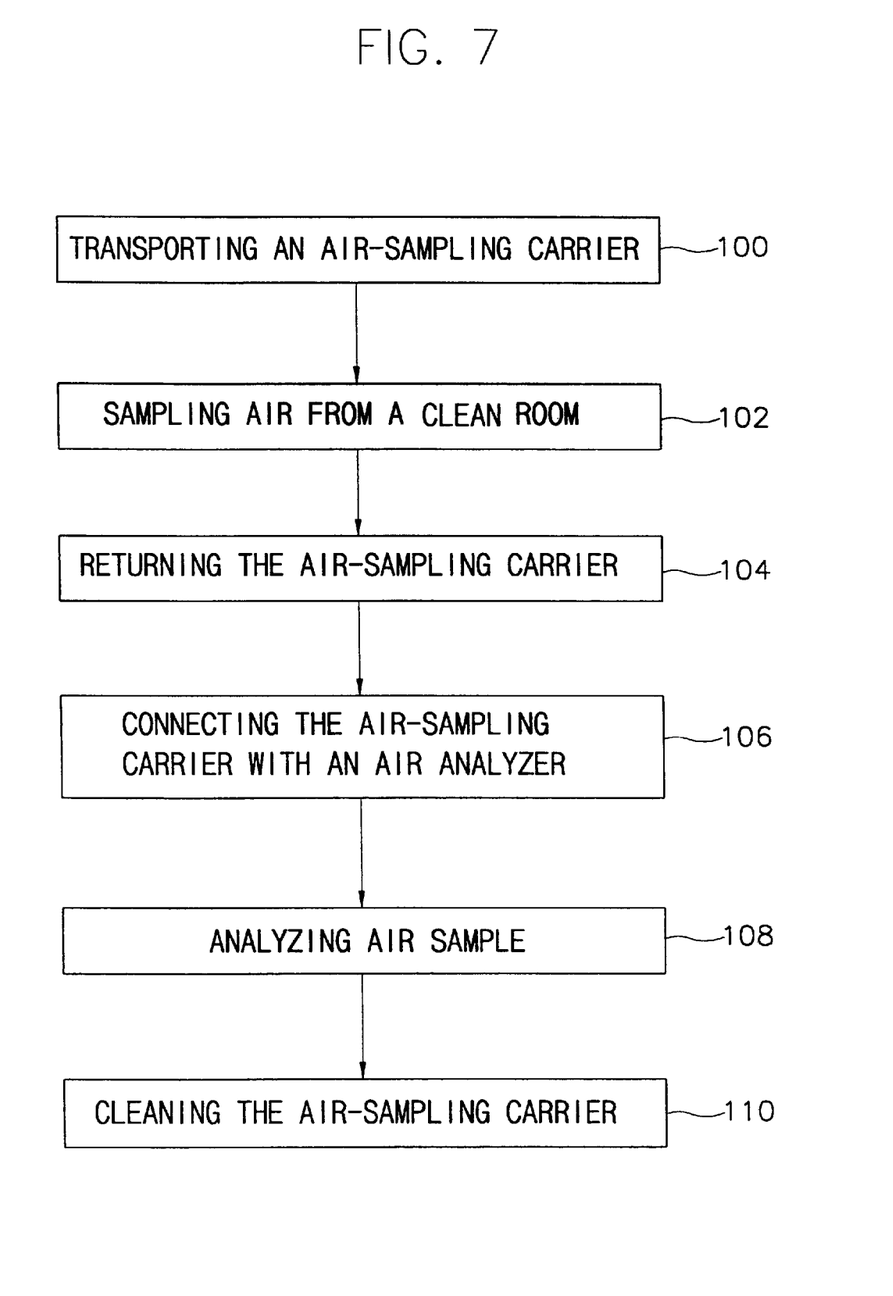
FIG. 7 illustrates a flowchart of a method for analyzing the air according to an embodiment of the present invention.

Operation of an embodiment of the present invention described above will now be described with reference to FIG. 7.

Firstly, in step 100, the system controller controls the unmanned carrier to transport the air-sampling carrier to the respective unit process tools of which the pollution level is to be measured.

The unit process tool opens the door of the air-sampling carrier using the door opener so that the air in the clean room is moved to the air-sampling carrier to be charged in the inner space of the air-sampling carrier over time. The unit process tool operates the door opener to close the door of the air-sampling carrier after a predetermined amount of time. Thereby, completing the sampling of the air of step 102.

In step 104, when the unit process tool transfers a signal to the system controller that the door is closed, the system controller allows the unmanned carrier to transport the air-sampling carrier to the air analyzer and gives the air analyzer information of the movement of the air-sampling carrier.

In step 106, the air analyzer connects the sample port line and the purge gas supplying line to the discharging pipe and the inlet tubes of the air-sampling carrier, respectively.

In step 108, the air analyzer analyzes the pollution level of the air sample while the purge gas is supplied through the purge gas supplying line to the inner space of the air-sampling carrier and the air sample and the purge gas are provided through the sample port line to the analyzer.

In step 110, when finished analyzing the air sample, the analyzer separates the sample port line from the discharging pipe and supplies the purge gas through the purge gas supplying line to the inner space of the air-sampling carrier to clean and charge the inner space of the air sample carrier with the purge gas. Then, the operation of sampling air is performed again, and the steps are repeated.

In the above description of an embodiment of present invention, only OHT (overhead transfer) is described with relation to the unmanned carrying apparatus, but the unmanned carrying apparatus may include an AGV (automatic guided vehicle).

Furthermore, the discharging pipe and the inlet tubes are installed on the upper surface of the air-sampling carrier in this embodiment of the present invention, but installation position of the discharging pipe and the inlet tubes is not limited to the upper surface of the air-sampling carrier.

For example, the discharging pipe and the inlet tubes may be installed on a bottom surface of the air-sampling carrier, while the sample port line and the purge gas supplying line are installed on the support of the air analyzer so that the discharging pipe and the inlet tubes are respectively and automatically connected to the sample port line and the purge gas supplying line when the air-sampling carrier is placed on the support.

According to the present invention, unmanned semiconductor fabricating facilities using the closed type wafer carrier use the air-sampling carrier to measure the pollution level in the clean room of the unit process tools instead of using a plurality of sensors for measuring the pollution level. The unmanned carrying apparatus carries the air-sampling carrier to take air samples in the respective unit process tools, and then the air analyzer analyzes the air samples. Accordingly, the pollution level in the Mini-environment clean rooms may be simply and easily measured, and a cost for installing the sensors may be saved. Furthermore, since the sensors are not needed, maintenance and repair for the semiconductor fabricating facilities are reduced.

Preferred embodiments of the present invention have been disclosed herein and, although specific terms are employed, they are used and are to be interpreted in a generic and descriptive sense only and not for the purpose of limitation. Accordingly, it will be understood by those of ordinary skill in the art that various changes in form and scope may be made without departing from the spirit and scope of the present invention as set forth in the following claims.

What is claimed is:

1. An apparatus for analyzing air for use in semiconductor fabricating facilities having a closed type wafer carrier, a plurality of respective unit process tools for opening and closing a door of the closed type wafer carrier and for loading and unloading wafers, and an unmanned carrying apparatus for carrying the closed type wafer carrier to the respective unit process tools, comprising:

an air-sampling carrier for sampling air inside the respective unit process tools having an external appearance similar to that of the closed type wafer carrier to facilitate being carried by the unmanned carrying apparatus; and an air analyzer for analyzing the air inside the air-sampling carrier in order to measure a pollution level of the air from inside the respective unit process tools sampled by the air-sampling carrier.

2. The apparatus for analyzing air for use in semiconductor fabricating facilities as claimed in claim 1, wherein the external appearance of the air-sampling carrier is that of a FOUP (front opening unified pod) standard.

3. The apparatus for analyzing air for use in semiconductor fabricating facilities as claimed in claim 2, wherein the air-sampling carrier comprises:

a container having an inner space;

a door mounted at a front wall of the container;

a discharging pipe, which is formed on an outer surface of the container and is connected to an inner space of the container, for discharging sampled air out of the container; and at least one inlet tube, which is formed on the outer surface of the container and connected to the inner space of the container, for introducing purge gas into the inner space of the container from outside the container.

4. The apparatus for analyzing air for use in semiconductor fabricating facilities as claimed in claim 3, wherein the air analyzer comprises:
- a support for supporting the air-sampling carrier;
- a sample port line connected to the discharging pipe of the air-sampling carrier placed on the support to introduce the sampled air therein;
- a purge gas supplying line connected to at least one inlet tube of the air-sampling carrier placed on the support to supply the purge gas to the air analyzer; and
- an analyzer connected to the sample port line for analyzing the pollution level of the sampled air.

5. The apparatus for analyzing air for use in semiconductor fabricating facilities as claimed in claim 4, wherein the air analyzer measures the pollution level of the sampled air while receiving the sampled air and the purge gas introduced through the sample port line during an injection of the purge gas into the air-sampling carrier through the purge gas supplying line after the sample port line and the purge gas supplying line are respectively connected to the air-sampling carrier, and then after measuring the pollution level of the sampled air, disconnects the sample port line from the air-sampling carrier and injects the purge gas having a pollution level of zero into the air-sampling carrier through the purge gas supplying line.

6. The apparatus for analyzing air for use in semiconductor fabricating facilities as claimed in claim 4, wherein the air analyzer calculates the pollution level of the respective unit process tools, which is determined by the following equation:

$$\text{pollution level of the respective unit process tools} = \frac{a \times (b+c)}{d}$$

where a denotes a pollution level in the air analyzer, b denotes a volume of the air-sampling carrier, c denotes an injection volume of the purge gas, and d denotes a volume of the air-sampling carrier.

7. An air-sampling carrier for collecting an air sample from one or more unit process tools used in semiconductor fabricating facilities comprising:
- a container having an inner space;
- a door mounted at a front wall of the container;
- a discharging pipe, which is formed on an outer surface of the container and is connected to an inner space of the container, for discharging the sampled air out of the container; and
- at least one inlet tube, which is formed on the outer surface of the container and connected to the inner space of the container, for introducing purge gas into the inner space from outside the container.

8. The air-sampling carrier for collecting an air sample in semiconductor fabricating facilities as claimed in claim 7, wherein the discharging pipe is disposed at a position adjacent to the door and at least one inlet tube is disposed at a position adjacent to a back surface of the container.

9. The air-sampling carrier for collecting an air sample in semiconductor fabricating facilities as claimed in claim 8, wherein two inlet tubes are installed at two corners near the back surface of the container.

10. A method of analyzing air in semiconductor fabricating facilities comprising:
- transporting an air-sampling carrier by means of an unmanned carrying apparatus to a respective unit process tool in which the air is to be sampled;
- sampling the air in the respective unit process tool by introducing the air into an inner carrier of the air-sampling carrier after opening a door of the air-sampling carrier;
- transporting the air-sampling carrier to an air analyzer by means of the unmanned carrying apparatus;
- connecting a sample port line and a purge gas supplying tube of the air analyzer to the air-sampling carrier;
- analyzing a pollution level of the sampled air after introducing the sampled air and purge gas into the air analyzer through the sample port line while injecting the purge gas into an inner space of the air-sampling carrier through the purge gas supplying line; and
- providing the inner space of the air-sampling carrier with a purge gas having a pollution level of zero through the purge gas supplying line after disconnecting the sample port line from the air-sampling carrier when the analyzing is finished.

11. The method of analyzing air in semiconductor fabricating facilities as claimed in claim 10, wherein the air analyzer calculates the pollution level of the respective unit process tools, which is determined by the following equation:

$$\text{pollution level of the respective unit process tools} = \frac{a \times (b+c)}{d}$$

where a denotes a pollution level in the air analyzer, b denotes a volume of the air-sampling carrier, c denotes an injection volume of the purge gas, and d denotes a volume of the air-sampling carrier.

* * * * *